United States Patent [19]
Tendler et al.

[11] Patent Number: 5,730,984
[45] Date of Patent: Mar. 24, 1998

[54] VACCINE AGAINST HELMINTH INFECTION COMPRISING SM-14 FATTY ACID BINDING PROTEIN OF *SCHISTOSOMA MANSONI*

[75] Inventors: Miriam Tendler, Rio de Janeiro; Naftale Katz; Andrew John Simpson, both of Belo Horizonte, all of Brazil

[73] Assignee: Fundacaco Oswaldo Cruz-Fiocruz, Rio de Janeiro, Brazil

[21] Appl. No.: 554,463

[22] Filed: Nov. 7, 1995

Related U.S. Application Data

[63] Continuation of Ser. No. 178,555, Jan. 6, 1994, abandoned.

[30] Foreign Application Priority Data

Dec. 16, 1993 [BR] Brazil .................................. 9305075

[51] Int. Cl.⁶ .......................... A61K 39/00; A61K 38/16
[52] U.S. Cl. ................................. 424/191.1; 424/192.1; 424/266.1; 930/210; 435/69.3
[58] Field of Search .................... 514/2, 12; 435/7.1, 435/7.22, 69.3; 530/350; 935/65; 424/185.1, 191.1, 192.1, 265.1, 266.1; 930/210

[56] References Cited

U.S. PATENT DOCUMENTS 4,396,600  8/1983  Messineo et al. .................. 424/88
5,219,566  6/1993  Strand .

FOREIGN PATENT DOCUMENTS 0554064  8/1993  European Pat. Off. .
90/02563  3/1990  WIPO .

OTHER PUBLICATIONS

Stanberry, L.R. 1991, Reviews of Infectious Diseases vol. 13 (Suppl. II) pp. 5920–5923.

Tendler et al. "The Presence of *Schistosoma mansoni* Antigens in Solutions Used for Storing Adult Worms", Revista do Instituto de Medicina Tropical de Sao Paulo, 21(6), pp. 293–296, Nov. 1979.

Tendler et al, "Immunogenic and Protective Activity of an Extract of *Schistosoma mansoni*", Memorias do Instituto Oswaldo Cruz, 77(3) pp. 275–283, Jul. 1982.

Tendler et al, "*Schistosoma mansoni*: Vaccination With Adult Worm Antigens", International Journal of Parasitology 16(4), pp. 347–352, 1986.

Tendler et al "*Schistosoma mansoni*: Protective Antigens", Memorias do Instituto Oswaldo Cruz, 82 (Suppl. IV) pp. 125–128, 1987.

Tendler et al "Vaccination in Murine Schistosomiasis With Adult Worm Derived Antigens: Variables Influencing Protection in Outbred Mice", Int. Journal for Parasitology 21(3) pp. 299–306, 1991.

Tendler et al, "Vaccination in Murine Schistosomiasis With Adult Worm Derived Antigens II: Protective and Immune Response in Inbread Mice", Memorias do Instituto Oswaldo Cruz, 87 (Suppl. I) pp. 281–286, 1992.

Moser et al, "A 14 KDa *Schistosoma mansoni* Polypeptide is Momologous to a Gene Family of Fatty Acid-Binding Proteins", The Journal of Biological Chemistry, 166–(13), pp. 8447–8454, 1991.

Perez et al, "Fasciola Hepatica: Molecular Cloning, Nucleotide Sequence and Expression of Gene Encoding a Polypeptide Homologous to a *Schistosoma mansoni* Fatty Acid-Binding Protein", Journal of Experimental Parasitology 74(4), pp. 400–407, Jun. 1992.

Smithers et al, "Schistosomiasis in: Immunology of Parasitic Infections", Blackwell Scientific Scientific Publications, second edition, 1982, chapter 16, pp. 527–607.

Smithers, D.R., "Fasciolasis and Other Trematode Infections, in: Immunology of Parasitic Infections", Blackwell Scientific Publications, second edition 1982, Chapter 17, pp. 608–621.

Miriam Tendler, "Vaccination Against Schistosomiasis with new Recombinant Antigen: Sm 14", Abstract No. 16, International Symposium on Shcistosomiasis, Nov. 1993.

Cristiana Alves–Brito et al, "High Level Expression of Recombinant Sm14, A Potential Anti–Schistosome Vaccine Candidate, Using A T7 RNA Polynerase Expression System", Abstract 80, International Symposium on Schistosomiasis, Nov. 1993.

Almelda, M.S. et al, "*Schistosome mansoni* Sm14 recombinant antigen inducing protection against *Faciola hepatica* infection", Abstract No. 95, International Symposium on Schistosomiasis, Nov. 1993.

Goncalves, A., "Reactivity of Sera From Schistosomiasis Patients Against Fatty Acid Binding Protein From *S. mansoni*, Sm 14", Abstract No. 14, International Symposium on Schistosomiasis, Nov. 1993.

Vilar, M.M. et al, "Experimental Vaccination With Recombinant Antigen Sm 14: Variation of Size and Number of challenge Infections", Abstract No. 134, International Symposium on Schistosomiasis, Nov. 1993.

Dean, "Schistosoma and Related Genera: Acquired Resistance in Mice", Experimental Parasitology, 55.1 104 1983, pp. 1–104.

Pearce et al., "Induction of Protective Immunity Against *Schistosoma mansoni* By Vaccination With *Schistosome paramyosia* (Sm97), a Nonsurface Parasite Antigen", Proc. Natl. Acad. Sci. USA 85 (1988) pp. 5678–5682.

(List continued on next page.)

*Primary Examiner*—Mary E. Mosher
*Attorney, Agent, or Firm*—Cushman Darby & Cushman IP Group of Pillsbury Madison & Sutro LLP

[57] ABSTRACT

The present invention relates to helminthic derived antigenic material capable of inducing effective and long lasting protection against parasites, in particular to antigens that mediate protective immunity against helminths.

25 Claims, 13 Drawing Sheets

(3 of 13 Drawing(s) in Color)

OTHER PUBLICATIONS

Soisson et al., "Induction of Protective Immunity in Mice Using a 62–kDa Recombinant Fragment of a *Schistosoma mansoni* Surface Antigen", The J. of Immunology, vol. 149, No. 11, 1992, pp. 3612–3620.

Katz, "Chemotherapy of *Schistosomiasis mansoni*", 1977, pp. 1–70.

Andrade et al., "A Patologia Da Esquistossomose Mansoni No Coelho", Mem. Inst. Oswaldo Cruz, Rio de Janeiro, vol. 83(3):323–333, 1988.

Almeida et al., "Curative and Protective Activity in Rabbits After Reinfection with *Schistosoma mansoni*: A New Model of Immunity?", Research Notes, J. Parasitol, 75(2), 1989, pp. 308–310.

Tendler et al., "*Schistosoma mansoni*—New Zealand Rabbit Mode: Resistance Induced By Infection Followed By Active Immunization With Protective Antigens", The J. of Parasitology, vol. 77, No. 1, 1991, pp. 138–141.

Hillyer et al., "Induction of Immunity in Mice to *Fasciola hepatica* With a Fasciola/Schistosoma Cross–Reactive Defined Immunity Antigen", A. J. Trop. Med. Hyg. 34(6), 1985, pp. 1127–1131.

Hillyer et al., "Acquired Resistance to *Fasciola hepatica* in Cattle Using a Purified Adult Worm Antigen", Am. J. Trop. Med. Hyg. 37(2), 1987, pp. 363–369.

Nash et al., "Schistosome Infections in Humans: Perspectives and Recent Findings", Annals. of Internal Medicine, 1982:97:740–754.

Cherfas, "New Hope for Vaccine Against Schistosomiasis", Science, vol. 251, 1991, pp. 630–631.

Shoemaker et al., "cDNA Cloning and Functional Expression of the *Schistosoma mansoni* Protective Antigen Triosephosphate Isomerase", Proc. Natl. Acad. Sci. USA, vol. 89, 1992, pp. 1842–1846.

Smith et al., "Cross–immunity to *Schistosoma mansoni* and *S. haematobium* in the Hamster", Parasitology (1976), 73, pp. 53–64.

Goudot–Crozel et al., "The Major Parasite Surface Antigen Associated With Human Resistance to Schistosomiasis Is A 37–kD Glyceraldehyde–3P–Dehydrogenase", J. Exp. Med., vol. 170, 1989, pp. 2065–2080.

da Silva et al., "Molecular Cloning of a 16–kilodalton Cu/Zn Superoxide Dismutase from *Schistosoma mansoni*", Molecular and Biochemical Parasitology, vol. 52, 1992, pp. 275–278.

Smith et al., "Mr 26,000 Antigen of *Schistosoma japonicum* Recognized by Resistant WEHI 129/J Mice is a Parasite Glutathione S–transferase", Proc. Natl. Acad. Sci. USA, vol. 83, 1986, pp. 8703–8707.

Mitchell et al., "Sensitization Against the Parasite Antigen Sj26 is not sufficient for consistent expression of Resistance to Schistosoma . . . ", Trans. of the Royal Soc. of Trop. Med. and Hyg. vol. 82, 1988, pp. 885–889.

Mitchell et al., "Attempts to Induce Resistance in Mice to *Schistosoma japonicum* and *Schistosoma mansoni* by Exposure to Crude Schistosome Antigens . . . ", Immunol. Cell. Biol. vol. 68, 1990, pp. 377–385.

James et al., "The Influence of Adjuvant on Induction of Protective Immunity By a Non–Living Vaccine Against Schistosomiasis", The J. of Immun., vol. 140, 1988, pp. 2753–2759.

Bomford, "Adjuvants for Anti–parasite Vaccines", Parasitology Today, vol. 5, No. 2, 1989, pp. 41–46.

Steel et al., "CRC Handbook Series in Zoonoses", 1982, pp. 71–74.

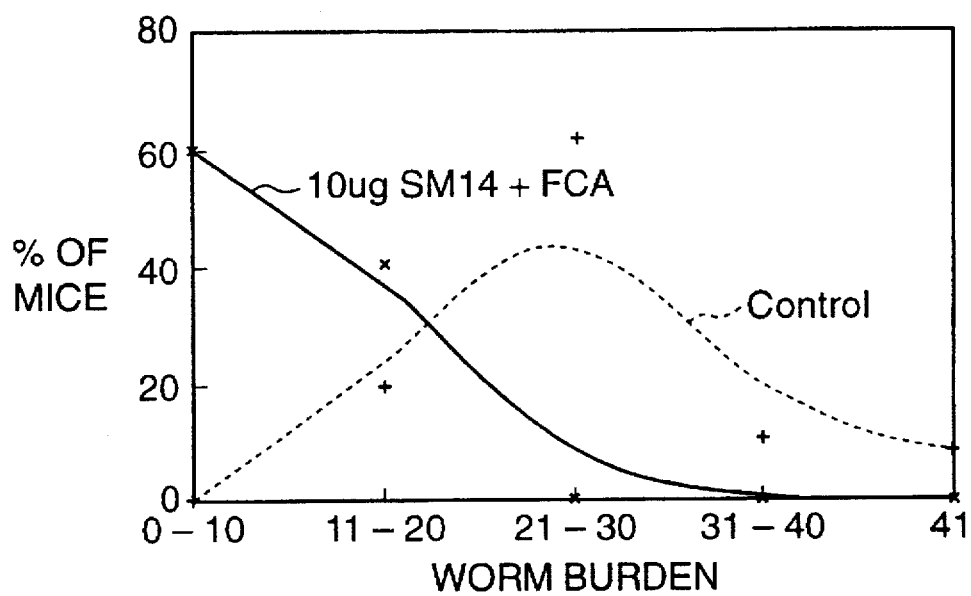
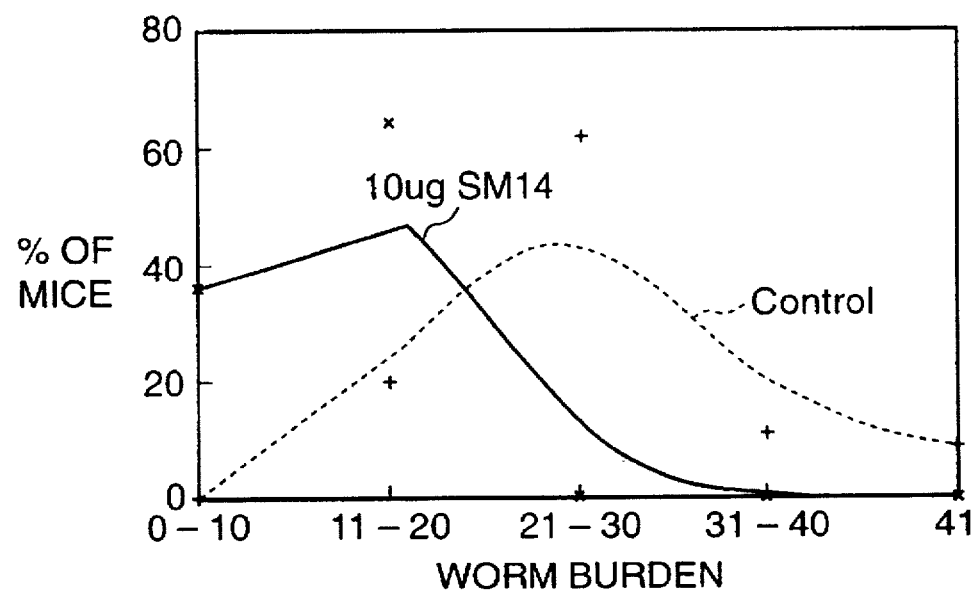

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: PROTEIN ( x i ) SEQUENCE DESCRIPTION: SEQ ID NO:1:

```
Met Ser Ser Phe Leu Gly Lys Trp Lys Leu Ser Glu Ser His Asn Phe
  1               5                  10                  15

Asp Ala Val Met Ser Lys Leu Gly Val Ser Trp Ala Thr Arg Gln Ile
             20                  25                  30

Gly Asn Thr Val Thr Pro Thr Val Thr Phe Thr Met Asp Gly Asp Lys
         35                  40                  45

Met Thr Met Leu Thr Glu Ser Thr Phe Lys Asn Leu Ser Cys Thr Phe
     50                  55                  60

Lys Phe Gly Glu Glu Phe Asp Glu Lys Thr Ser Asp Gly Arg Asn Val
 65                  70                  75                  80

Lys Ser Val Val Glu Lys Asn Ser Glu Ser Lys Leu Thr Gln Thr Gln
                 85                  90                  95
```

-continued

```
Val Asp Pro Lys Asn Thr Thr Val Ile Val Arg Glu Val Asp Gly Asp
            100                 105                 110

Thr Met Lys Thr Thr Val Thr Val Gly Asp Val Thr Ala Ile Arg Asn
            115             120                 125

Tyr Lys Arg Leu Ser
    130
```

VACCINE AGAINST HELMINTH INFECTION COMPRISING SM-14 FATTY ACID BINDING PROTEIN OF *SCHISTOSOMA MANSONI*

This is a continuation of application Ser. No. 08/178,555, filed on Jan. 6, 1994, which was abandoned.

BACKGROUND OF THE INVENTION

This invention relates in general to helminthic derived antigenic material capable of inducing effective and long lasting protection against parasites, in particular to antigens that mediate protective immunity against helminths.

Among the helminths, the digenetic trematodes or flukes, comprise over 100 families. The majority are comparatively harmless parasites living in the intestine and other organs of vertebrates and accordingly have received scant attention from applied parasitologists. Those trematodes which cause serious disease in man are the blood flukes or schistosomes and the liver flukes and lung flukes which are very important parasites that infect animals.

Fasciola the most important of the liver flukes is principally parasitic in domestic ruminants and is responsible for serious economic loss throughout the world (cattle, sheep and goats).

The main characteristic of the disease and one, which is responsible for pathology, morbidity and mortality of the mentioned animals, is the destruction of the host's liver tissue and damage to the bile ducts. Morbity is higher in young animals that are especially affected and become emaciated and die. Fasciola can also parasitize man, when given the opportunity and it is more frequent in Cuba and Latin America countries. Nevertheless, the true human liver fluke is another parasite, namely the *Clonorchis sinensis*, which is widespreach in China, Japan, Korea, Vietnam and India. Pathology is basically caused by thickening of bile duct walls and in severe cases cirrhosis of the liver and death.

Both Fasciola and Clonorchis gain entry passively as metacercariae ingested with food (herbage and raw fish for Fasciola and Clonorchis respectively) but their route of migration in the vertebrate's host body to the bile ducts differs.

While Clonorchis arrises in the bilary tree from the intestine through the ampulla of Vater, Fasciola migrates across the abdominal cavity, penetrating successively the intestine wall and liver parenchryma, causing more serious damage to host tissues.

As regards Fasciolosis in domestic animals, there are conflicting results and poor evidence to suggest that sheep or goats acquire immunity against *Fasciola hepatica* (Sinclair, 1967) after immunization with crude extracts.

There are also evidences to show that infection can persist for at least 11 years in experimentally infected sheep. (Durbin, 1952). It is also reported that very little or no reaction of the host against the parasite occurs; thus the survival of the sheep will depend entirely upon the number of metacercariae ingested (Boray, 1969). Cattle are considered to be more resistant: *F. hepatica* generally lives in this host from 9–12 months but it is the young calves that present the more severe clinical fasciolosis.

Several attempts have been made to identify immunoprophylatic antigens that could provide good basis for developing efficient vaccine against Fasciolosis. Basically two independent experimental strategies have ben pursed by several scientists based on: 1) immunity induced by irradiated live vaccines and 2) immunity induced by non-living vaccines.

Nevertheless, few attempts have been published on acquired resistance to *Fasciola hepatica* in calves using somatic fluke extracts (Ross, 1967; Hall and Lang, 1978, Hillyer, 1979) and they reported conflicting data.

Immunity induced by irradiated live vaccines has also showed frustrating results in experiments performed in mice, rabbits or sheep (Campbell et al., 1978, Hughes 1963); since there is no evidence of immunity developing in these animals following administration of irradiated metacercariae.

In addition, experiments with different extracts or excretory/secretory products from adult bile stage flukes were not immunogenic, providing that vaccinated animals presented low protection and pathological lesions in the liver parenchryma.

As reflected in the previous state of the art, it is expected that cattle would respond better to vaccination with non-living vaccines, but it was doubtful whether similar predictions could be made for sheep, on the basis of only mediocre protection induced by a number of different antigens in experimental animals.

The induction of protective immunity against *F. hepatica* by means of heterologous immunity has also been envisaged. Campbell et al (1977) showed that infection of sheep with *Cysticercus tenuicollis*, that is the metacestode stage of the dog tapeworm *Taenia hydatigena*, produced partial protection against *F. hepatica*, but Hughes et al. (1978), however, could not confirm this result. Other experiments were also unable to induce protection against *Fasciola hepatica* in experimental animals with this tapeworn.

Mice infected with bisexual adults of *S. mansoni* developed statistically significant resistance to *F. hepatica* and simultaneous infections with both parasites resulted in a reduced number of established schistosomes and reduced schistosome egg production per worm (Christensen et al. 1978). Calves infected with *S. bovis* also showed some resistance to *F. hepatica* and less pronounced liver tissue damage (Sirag et al. 1981).

Pelley and Hillyer, 1978, Hillyer and de Atica 1980, reported common antigens between *F. hepatica* and *Schistosoma mansoni* found in the Schistosoma egg. Another finding that indicates cross reactive immunity is the occurrence of false positive reactions in areas were both parasites are endemic. Hillyer, 1985 and Hillyer et al 1987, demonstrated also that a mixture of antigens derived from *Fasciola hepatica* can confer protection against subsequent infection with both *F. hepatica* and *Schistosoma mansoni*.

Schistosomisasis or Bilharzia is an ancient water-borne disease recorded by the Egyptians 4000 years ago and is today a world-wide public health problem estimated to afflict more than 200 million people in urban and peri-urban areas of the Third World. The three principal schistosomes infecting man are transmitted by freshwater snails and the free-swimming larvae, called cercariae, which are shed into the water and are able to penetrate host skin directly. After migration from the dermis through the lungs to the hepatic portal system, the schistosomes come to live in the small mesenteric or pelvic veins, where each female lays upwards of 100 eggs per day into the bloodstream. The host's immune reaction to those eggs which become lodged in the tissues is largely responsible for the chronic debilitating and often fatal disease. The extension of irrigation schemes, the construction of dams and the concentration of human populations are today contributing to the increase in the distribution and intensity of schistosome infection. Snail control and chemotherapy are the principal, but by no means satisfactory methods of control. An efficient vaccine would be the ultimate goal to aid considerably in the attempts to eradicate the disease.

A variety of host species can develop partial resistance to *Schistosopma mansoni* following prior infection or immunization with radiation attenuated cercariae (Smithers & Doenhoff, 1982). The prior status of remission regarding the possibility to experimentally immunizing against *S. mansoni* infection (Clegg & Smith, 1978) has been replaced by the current enthusiasm for the possibility of producing a defined and effective vaccine against this parasite with dead vaccines (Tendler, 1987). Nevertheless the major limitation remains the incomplete degree of protection achieved in animals in most experiments with purified and chemically defined parasite antigens. As described by several authors and reviewed by Smithers, 1982 there was a general consensus on the need to increase the level of protection induced by experimental immunoprophylaxis. However, the establishment of a good animal model for the development of an efficient vaccine against schistosomiasis, has been very hard to achieve. Progress is dependent on the identification and purification of highly effective antigenic molecules that would mediate protective immunity. (*Schistosoma mansoni*: Protective Antigens, M. Tendler—Mem. Inst. Oswaldo Cruz. Rio de Janeiro, Vol. 82, Suppl. IV: 125–128, 1987).

In previous studies on the search of antigens that mediate protective immunity against schistosomes, we reported on the use of a "cocktail" of schistosome components (called SE) early released during incubation of live and freshly perfused *S. mansoni* adult worm in phosphate buffered saline (Tendler & Scapin, 1979; Kohn et al, 1979). Focusing on attempts to achieve protection against cercarial infection using as a vaccine, an experimental model was designed, in two different outbred animal hosts, the SW mouse and NZ rabbits, known to be fully susceptible and partially resistant to *S. mansoni* infection respectively.

In the New Zeland rabbit *S. mansoni* model, it was possible to establish a reliable pattern of percutaneous infections, with rather homogeneous adult worm loads, in terms of number and size of parasites and male/female ratios, for a long period after infection (Tendler, 1982, 1985, 1986). Recent evidence suggests that the use of the rabbit as an experimental host for *S. mansoni* may represent a new model of immunity for the disease (Almeida et al., 1987).

Immunization experiments performed in rabbits, with the SE mixture, resulted in very high levels of protection upon challenge (Scapin et al., 1980; Tendler, 1980; Tendler et al., 1982) (90% mean worm burden reduction in immunized animals compared to sex and age matched normal controls, when challenged simultaneously with the same number and pool of active cercariae from the —LE strain of *S. mansoni*). SW mice immunized with SE, have also shown to be significantly protected against challenge with normal cercariae and fully resistant to lethal infection (Tendler, 1986). To measure resistance, vaccinated and challenged animals, and the controls in parallel are submitted to hepatic and mesenteric perfusion for determination of adult parasite loads. The degree of protection is calculated by the difference in number of parasites recovered from control versus vaccinated animals (Tendler et al., 1982).

In the light of in vitro evidences that antibodies formed against different developmental stages of the parasite are effective in eosinophil or complement dependent cytotoxicity assays (Grzych et al., 1982; Smith et al., 1982), the characterization of antigens recognized by sera from demonstrably immune hosts, is used to identify antigenic molecules concerned with protective immunity (Bickle et al., 1986; Horowitz & Arnon, 1985). Western blot experiments were undertaken to analyse the antibody response of SE vaccinated rabbits. Probing SE antigens with a panel of anti-sera derived from rabbits immunized by the same scheme (SE-FCA), the authors were able to demonstrate in immunoblots, two distinct patterns of recognition of SE antigens in these individuals. Interestingly, some SE antigens were restrictedly recognized only by anti-sera from almost fully protected rabbits. This finding enabled the authors to identify two subsets of antigens in SE; one common to all individual rabbit antisera, and a second subset restricted to highly protected animals. Those two patterns were respectively named Low and High protection patterns and used as "differential" antibodies. Taking advantage of these two patterns of recognition of SE components by polyclonal antibodies from rabbits that responded "differentially" to the same immunization scheme, (probably on account of individual variation, expected to occur in outbred populations), the strategy of screening cDNA libraries with those sera was applied. With the constraint of the incomplete understanding of critical mechanisms of protective response in both experimental and human schistosomiasis, screening procedures adopted by others frequently involved the use of infected human sera ("putative" immune or "susceptible" individuals of endemic areas [Carter & Colley, 1986] or selected monoclonal or polyclonal sera from immunized animals [Lanar et al., 1986; Balloul et al., 1987]), that are directed against several non-characterized antigens.

In initial attempts towards the molecular cloning of potentially protective SE components, two cDNA libraries from whole adult worms of *S. mansoni* and *S. japonicum* constructed by Drs. Klinkert, University of Heidelberg and Donnelson/Henkle, Iowa University, respectively, were screened, with duplicate filters by differential screening. A parallel could be drawn with the results of immunoblots in that of two different sets of clones were detected, which presumably corresponds to the different in recognition by susceptible and resistant rabbit anti-SE sera. In additional experiments aiming at the identification of SE components, we compared in immunoblots, rabbit polyclonal anti-SE sera (High and Low protection) with a rabbit antiserum to purified schistosome paramyosin (kindly provided by Dr. A. Sher. NIH). This protein is a recently defined molecule, partially protective against *S. mansoni* challenge infection in inbred mice (Lanar et al., 1986), of Mr $(x10^{-3})$97, shown to be sensitive to proteolytic degradation to two major breakdown products of Mr $(x10^{-3})$ 95 and 78 (Pearce et al., 1986).

The 97/95/78 kD complex was recognized by both High and Low protection anti-SE sera and monospecific antiparamyosin sera. The "high" protection anti-SE sera recognized in addition to paramyosin, other polypeptides which remained to be well characterized and assessed in terms of their protective activity and immunological role. The finding of paramyosin as a component of SE, reinforces previous indirect immunofluorescence studies performed on sections of adult schistosomes with rabbit anti SE sera, that reacted with eggs on the parasite surface and in between the muscle layers (Mendonca et al., 1987), in a similar fashion as demonstrated for paramyosin (Pearce et al., 1986). This finding, also paralleled results of immunoscreening of cDNA libraries performed, as mentioned above. Again, common paramyosin clones were isolated with both anti-paramyosin and anti-SE sera, with extra clones being recognized only by the latter rabbit sera (High protection). Among the other SE components of lower molecular weight, the 31/32 KD doublet, described as potential candidates for diagnosis of schistosomiasis (Klinkert et al., 1987) and recently identified as proteases located in the schistosome gut were also identified (Klinkert et al., 1988). These antigens and others which were identified in the saline extract showed a very low protection when tested.

The incubation of freshly perfused schistosomes in a chemically defined media (PBS) was aimed at the extraction of early released antigens from live adult worms (specially excretory/secretory products and tegumental components). This strategy was adopted in view of former frustrating attempts to induce consistent resistance against schistosomotic infection with different crude extracts of S. mansoni, that theoretically could be depleted of relevant function antigens. This premise was mainly influenced by the extraction procedures commonly adopted, that derived from the use of dead parasites. In fact, using SE emulsified in FCA (as preferential adjuvant) and administered by the subcutaneous/intradermal route, we achieve a high and long term duration protection in two experimental animals hosts against S. mansoni infection. The rational for the use of the rabbit model, unusual for protection trials, was to achieve "tracking" potentially protective and discrete antigens in a partially resistant host (to be further tested in susceptible hosts) that could therefore "amplify" the immune response and effector mechanisms of parasite killing since rabbits are a known potent antibody producer, they were envisaged as an important tool in this respect.

Studies on the induced immune response in vaccinated animals aiming at the identification of the functional relevant SE protective components, site and mechanisms of parasite death and protection markers, were the focus of our efforts in recent years, but less information on the molecular composition of SE, as well as on the identification and isolation of its protective components was available until recently.

The U.S. Pat. No. 4,396,600 issued on Aug. 2, 1983 in the name of Luigi Messineo & Mauro Scarpin (according to Reexamination Certificate 461st B1 U.S. Pat. No. 4,396,000 issued on Feb. 11, 1986 it was cancelled) described an extract of adult Schistosome mansoni worms obtained by incubation in 0.15M sodium chloride-sodium phosphate buffer (pH 5.8) contains protein carboxydrates, and nucleic acid and or by-products of the latter component and resolves into four major fractions by gel chromatography in G-100 and G-200 Sephadex columns. Immunodiffusions tests with rabbit anti-total extract serum reveal three precipitation lines corresponding to fractions I and II and one with III or IV. Rabbits immunized with this total extract are found to be totally or partially (at least 77%) resistant to a challenge infection. The saline extract antigenic material is an effective vaccine for the treatment and immunization of schistosomiasis and other schistosome infection.

The official action mentioned above was based principally on two articles of the inventions and were used here as the principle of the present invention. Among the bulk of data that correspond to the background of present invention the most recent data were the cloning and sequencing of a SE derived component, identified as SM-14.

The most recent published study is "A 14-KDa Schistosoma mansoni Polypeptide is Homologous to a gene family of fatty Acid Binding Proteins—The Journal of Biological Chemistry—vol. 266, No. 13, Issue of May 5, pp. 8447–8454, 1991; D. Moser, M. Tendler, G. Griffiths, and Mo-Quen Klinkert". This study describes the sequencing of the gene and the demonstration of the functional activity of the Sm-14 as a protein which binds lipids to the Sm-14 structure.

SUMMARY OF THE INVENTION

This invention relates to an antigen to confer protective immunity against helminthic infections of humans and animals and the process of vaccination for immunoprophylaxis of helminthological diseases of veterinarian and human medical interest.

The object of the present invention is a vaccine against the infection caused by Fasciola hepatica in cattle, goats and sheep.

Another object of the present invention is a vaccine against infection caused by Schistosome mansoni and all others species of Schistosoma which are responsible for infections and disease in humans and animals.

Still another object of the invention is a vaccine against infection caused by all species of helminths of medical and veterinary interest.

Further object of the present invention is the use of the rSm 14 in the diagnostic of Schistosomiasis and Fasciolosis.

An additional objective is a method for developing a vaccine against the human Schistosoma by using the same vaccinating antigen in the immunoprophylaxis of diseases caused by different parasite species which affect humans and various animals.

A further objective is the Sm-14 molecule which has a tri-dimensional structure defined according to the present invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 4A, 4B, 4C and 4D show the evaluation of the level of protection of the rSm 14 according to experiment 2.

DETAILED DESCRIPTION OF THE INVENTION

Figure 1:
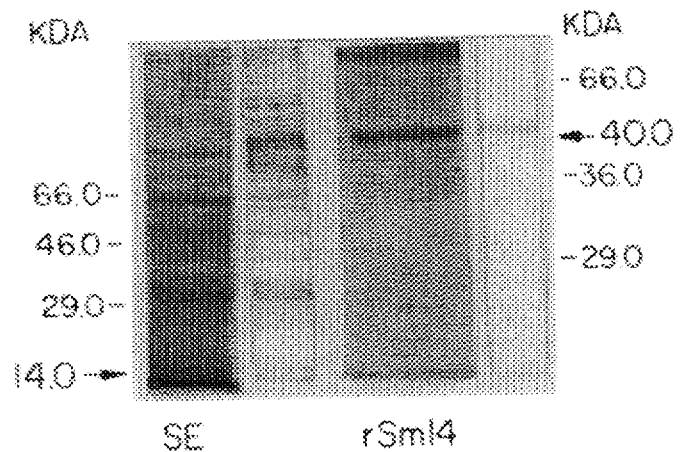
FIG. 1 shows a gel of the final antigen preparation (rSm 14 purification) in comparison with SE.

The method for developing a vaccine against the human Schistosoma species by using the same vaccinating antigen in the immunoprophylaxis of diseases caused by different parasite species which affect humans and various animals can be described through the following steps:

achieving the isolation of a common cross reactive antigen (which according to the preferred embodiment of the present invention is the Sm-14) which is highly protective against both a disease of animals and humans;

testing this antigen as a vaccine for the immunoprophylaxis of the disease of animals in experimental and definite hosts for the parasite which causes the infection and/or the disease;

analysing the information derived from vaccination of the animal host, namely domestic ruminants, focusing all related questions and prerequisites for the final development of a vaccine against given human disease such as toxicology and pathology.

Using the method according to the present invention it is possible to find an antigen which is simultaneously highly effective as a vaccine against two parasitic diseases, of both domestic animals and humans. According to the preferred embodiment of the present invention the parasitic diseases of both domestic animals and humans are Fasciolosis and Schistosomiasis respectively, as well as other helminthic diseases which affect specifically humans as different animal species.

One of the antigens in the complex SE mixture, Sm-14, has been cloned and exhibits a significant homology with fatty acid binding proteins and also with Fh 15, a *Fasciola hepatica* antigen. This cross reactive antigen namely Sm-14, in its recombinant form—r Sm 14 confers protective immunity against both Schistosomiasis and Fasciolosis.

We will demonstrate here the ability of a recombinant form of Sm-14 to confer a high protection against *Fasciola hepatica*, *Schistosoma mansoni*, as well as all other species of Schistosoma and Echeinococcus and putatively other helminths that are pathogenic to humans and animals. The levels of protection achieved from experimental vaccination of hundreds of animals, have shown that Sm-14 is a major protective molecule derived from SE and is the candidate for both an anti-schistosome vaccine and anti-Fasciola vaccine.

The present invention will now be described in terms of, but not limited to, the examples.

EXAMPLE 1

The procedure for obtaining, characterizing and purifying the recombinant Sm-14 is described below:

Phase 1:

The transition from the protective saline extract (SE) to the molecular vaccine was achieved as follows:

a) A LE strain λgt 11 cDNA library (prepared from the adult worms of the LE endemic strain of *Schistosoma mansoni*) was screened with immune serum anti-SE derived from fully protected individuals (namely rabbits and rabbit "High Protection" serum as previously described in this document).

b) one species of cDNA clone recognized by rabbit anti—SE high protection serum that provide highly intense signals, was selected among others.

c) the sequence and characterization revealed the protein of 14 KDa named Sm 14 (the nucleotide and deduced amino acid sequence is the already published work of Moser, Tendler et al.).

A practical example of how to conduct the production of the cDNA clone is described in the state of the art.

Phase 2:

Expression of Sm 14 in an efficient vector system

The method to conduct this up to PDS-14 is described in the state of the art (A 14-KDa *Schistosoma mansoni* Polypeptide Is Homologous to a gene Family of Fatty Acid Binding Proteins, The Journal of Biological Chemistry, Vol. 266, No. 13, Issue of May 5, pp. 8447–8454, 1991.) as well as the identification and results of cloned cDNA sequence and it is incorporated here for reference. The cDNA encodes a polypeptide having the amino acid sequence of SEQ ID NO: 1.

Antiserum produced in rabbits immunized with the schistosome extract was used to screen the adult *S. mansoni* cDNA library (previously described). A clone designated Sm-14 was plaque-purified after three rounds of immunoscreening. The recombinant phage was lysogenized in *E. coli* Y1089 and induced to express a beta-galactosidase-Sm 14 fusion protein of 122 KDa. The protein was purified by preparation SDS-polyacrilamide gel electrophoresis, and antibodies to the fusion protein were raised in a rabbit.

The subcloning of Sm-14 and its expression in the present vector in which the trials of vaccination against Schistosoma and Fasciola were made are described below:

Excising the entire open reading frame encoding for Sm-14 from the original construct pDS—Sm-14 by cleavage with Bam HI and Himd III.

The obtained fragment was ligated into pGEMEX-1 (Promega) cleaved with the same enzymes.

Phase 3:

The resulting construct which in turn, resulted in the gene being in frame for expression as a fusion protein with the T7 gene 10 protein, under the control of a T7 RNA polymerase promoter, was used to transform *E. coli* strain BL 21 (DE 3) which contains the gene for T7 RNA polymerase under control of lacUV. The *E. coli* strain BL21 (DE3) was used for expression of recombinant protein. Other strains of *E. coli* may be alternatively employed for the same purpose, as well as other systems of expression, e.g. PDS-14 as already in the state of the art.

Phase 4:

Colonies containing the recombinant plasmid were grown overnight, and the expression of T7 RNA polymerase induced by the addition of IPTG during subsequent log phase growth.

This procedure resulted in the expression of a fusion protein with predicted molecular weight of 40 KDA (14 KDa from Sm-14 and 26 KDa from the gene 10 protein).

Phase 5:

The bacterial cells were collected by centrifugation (5000 rpm/10 min) and resuspended in a lysis buffer (50 mM Tris-HCl, pH 7.5, 2 mM EDTA, 1 mM DTT, 2 mg/ml lysozyme) and incubate on ice for 15 minutes. The lysates were then sonicated for two 30 second cycles and recentrifuged. The pellet was resuspended in a washing buffer (50 mM Tris-HCl, pH 7.5, 10 mM EDTA, 1 mM DTT, 0.5% Triton x-100) and centrifuged.

Phase 6:

Following a further round of resuspension and centrifugation the final pellet was resuspended in water. A SDS-PAGE was then run, the antigen purified by electroelution and stored at temperatures ranging from −70° C. to −200° C. until use.

FIG. 1 shows the degree of purity of rSM 14 and the high efficiency of the expression.

Analysis of polyacrylamide gel electrophoresis of total *S. mansoni* SE antigens and purified Sm-14 transferred to nitrocellulose paper. Lanes 1–3, SE and Sm-14 resolved in 10 and 15% SDS-PAGE respectively stained with C. blue. Lanes 2 and 4 immunoblot. Lane 2 was probed with polyclonal antiserum from a rabbit immunized with SE. Lane 4, rabbit anti-Sm-14 fusion protein antiserum. Standard molecular low markers are show in both side of the figure.

Figure 2:
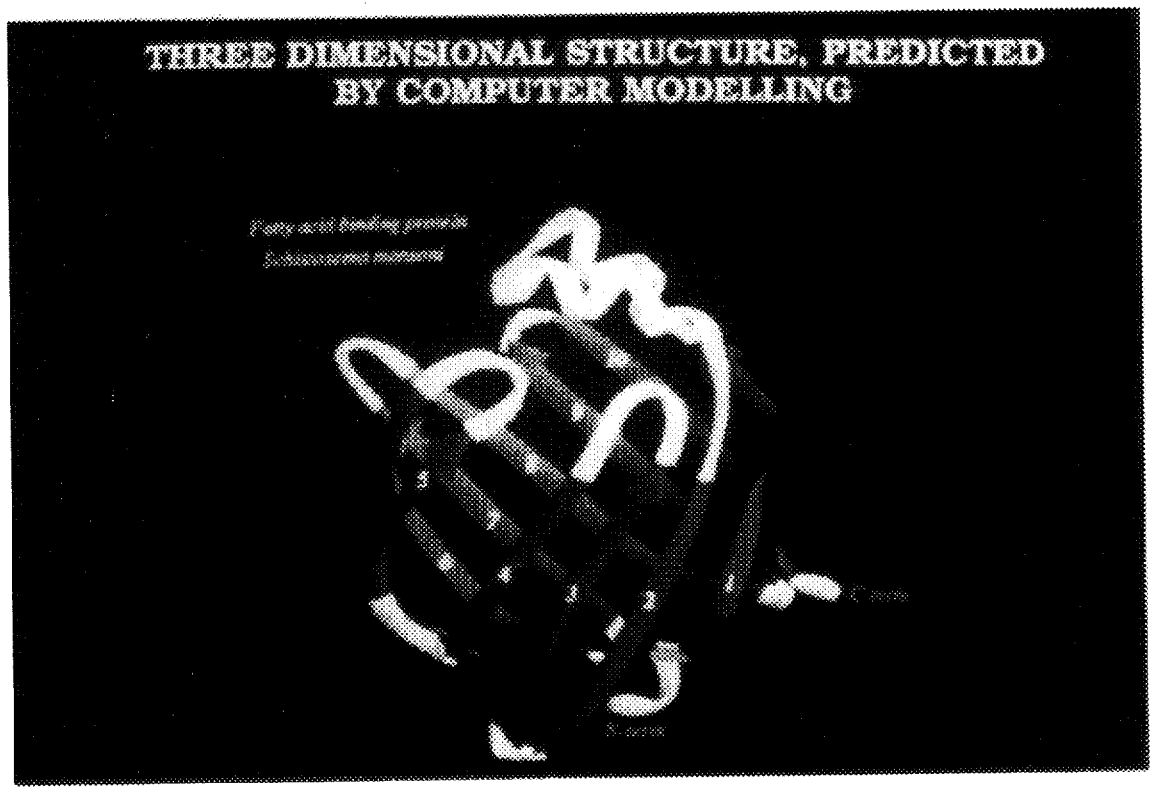
FIG. 2 shows the three dimensional structure of rSm 14 predicted by computer modelling.
Figure 3A:
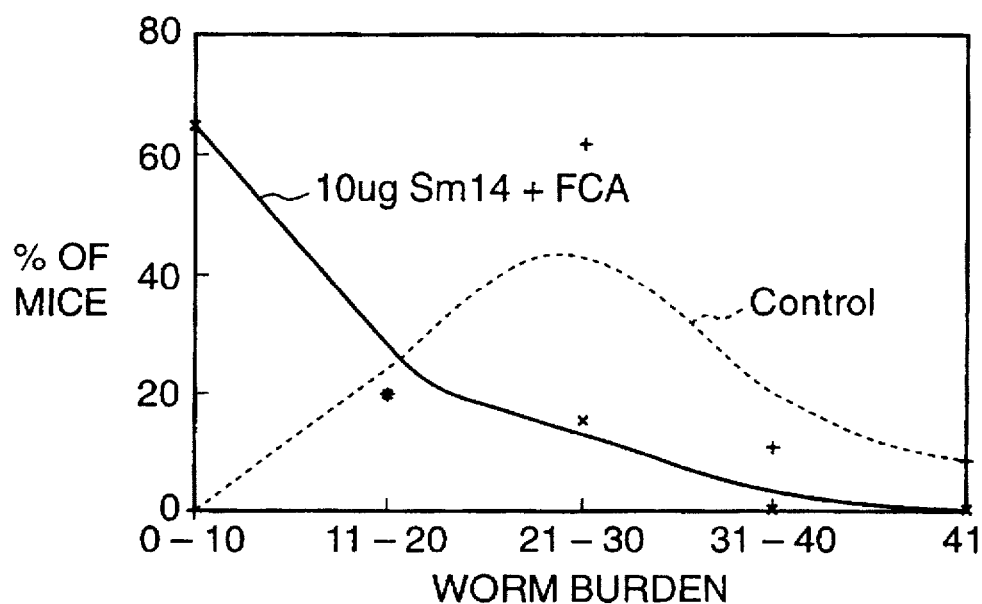
FIGS. 3A, 3B, 3C and 3D show the evaluation of the level of protection of the rSm 14 according to experiment 1.
Figure 3B:
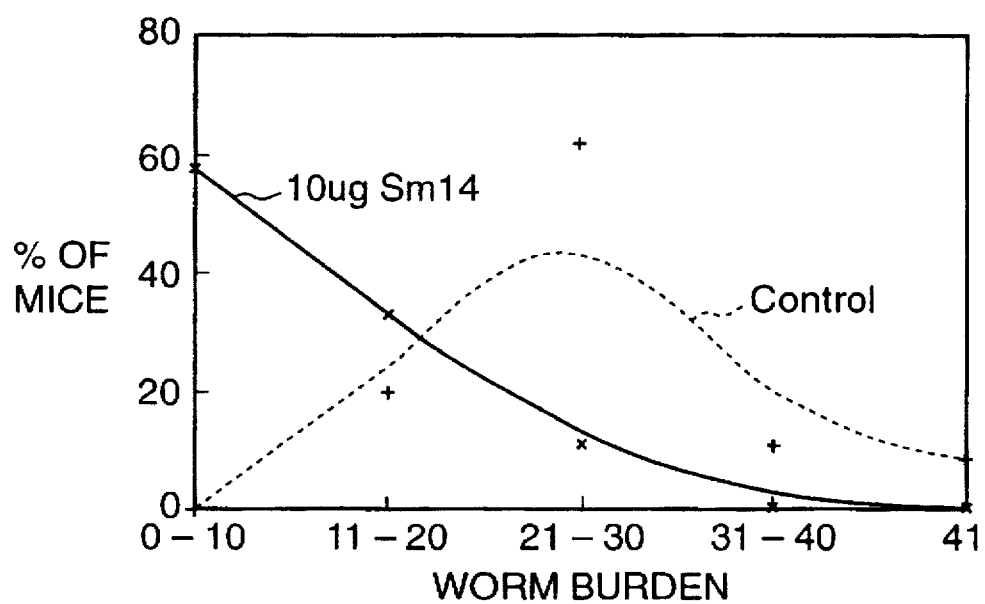
Figure 3C:
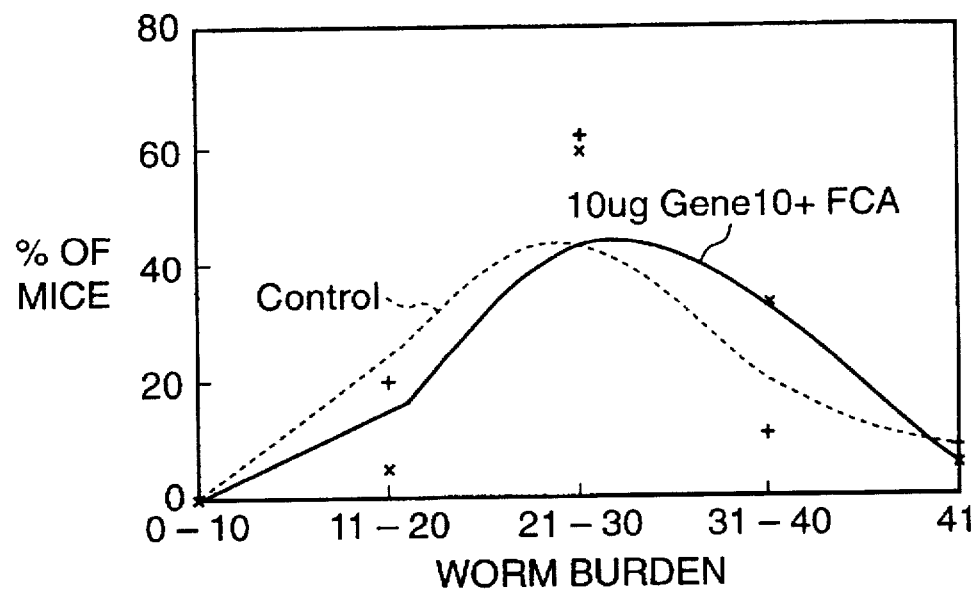
Figure 3D:
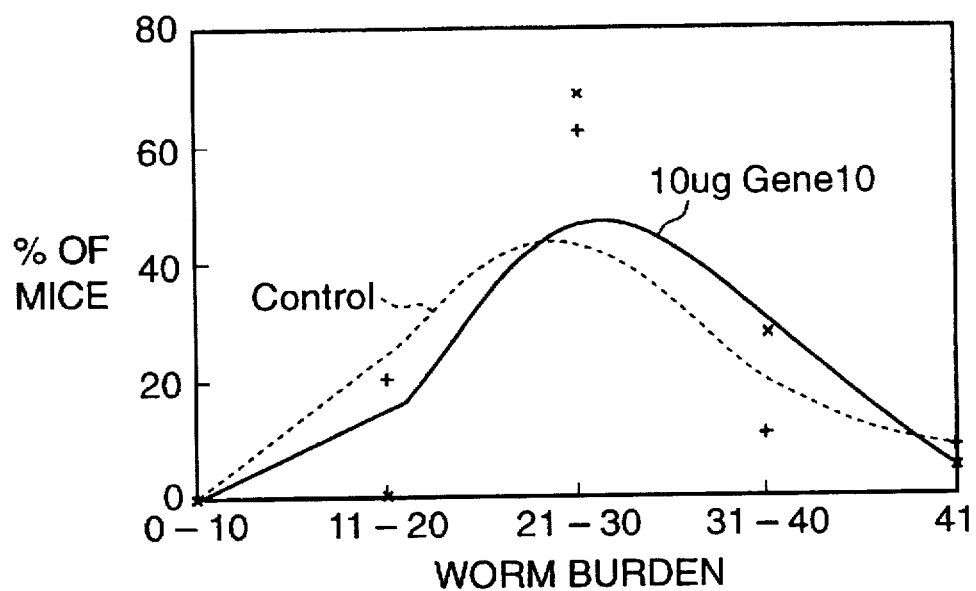
Figure 4A:
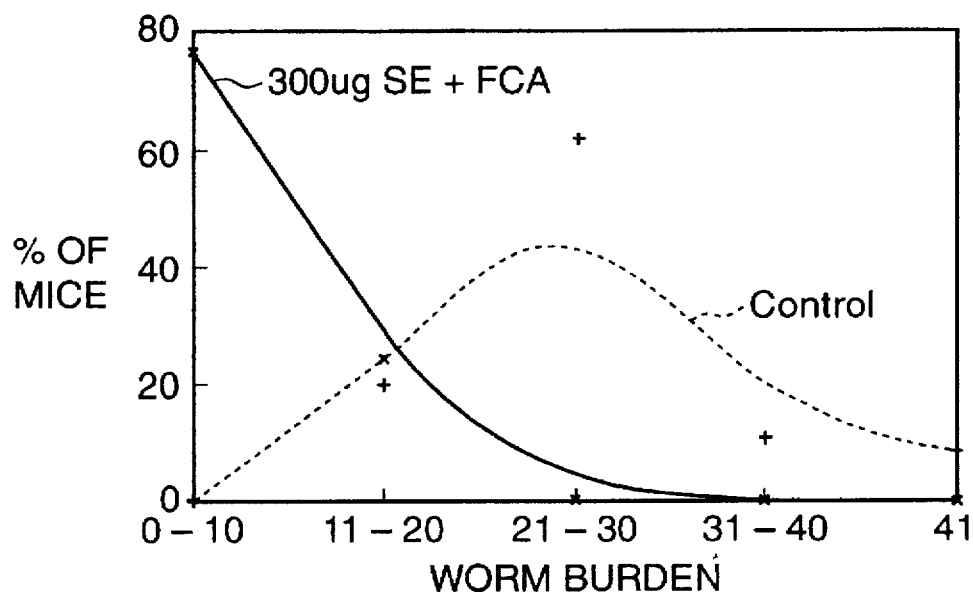
Figure 4B:
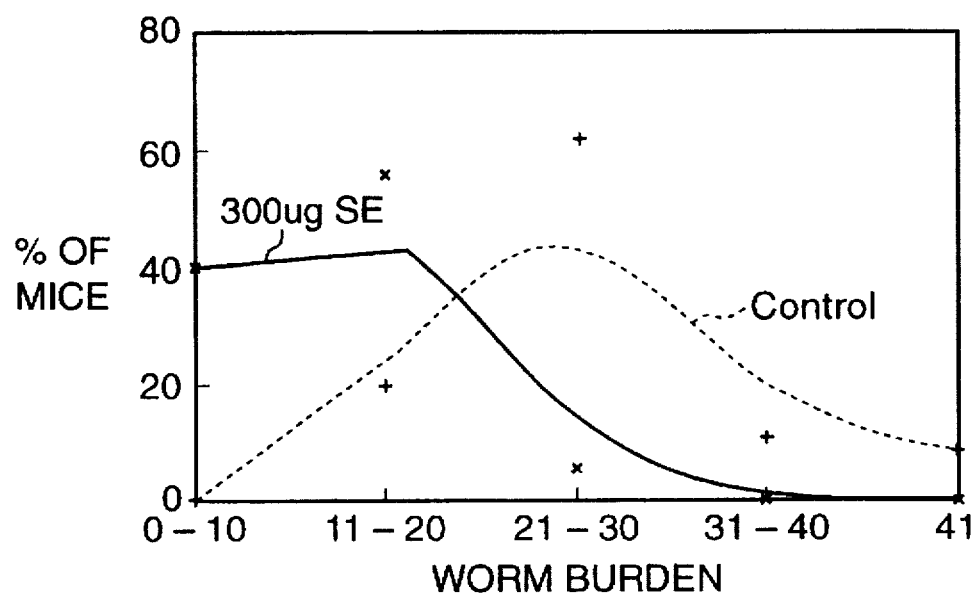
Figure 5A:
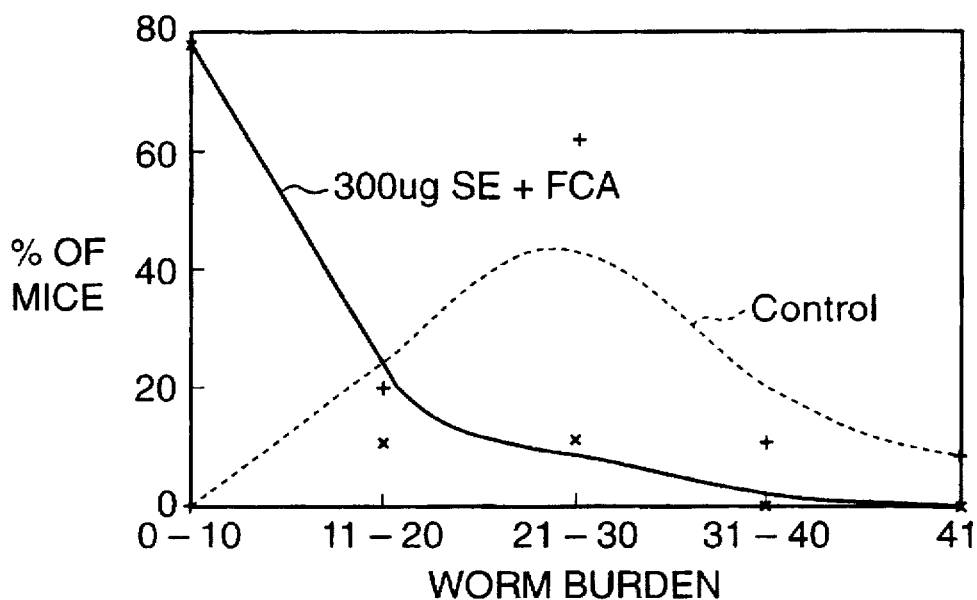
FIGS. 5A, 5B, 5C and 5D show the evaluation of the level of protection of the rSm 14 according to experiment 3.
Figure 5B:
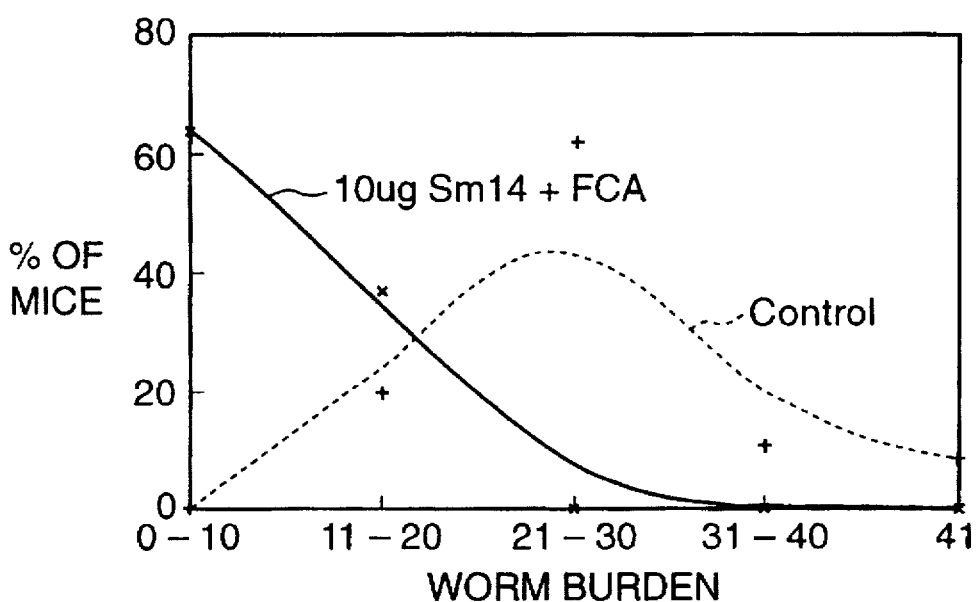
Figure 5C:
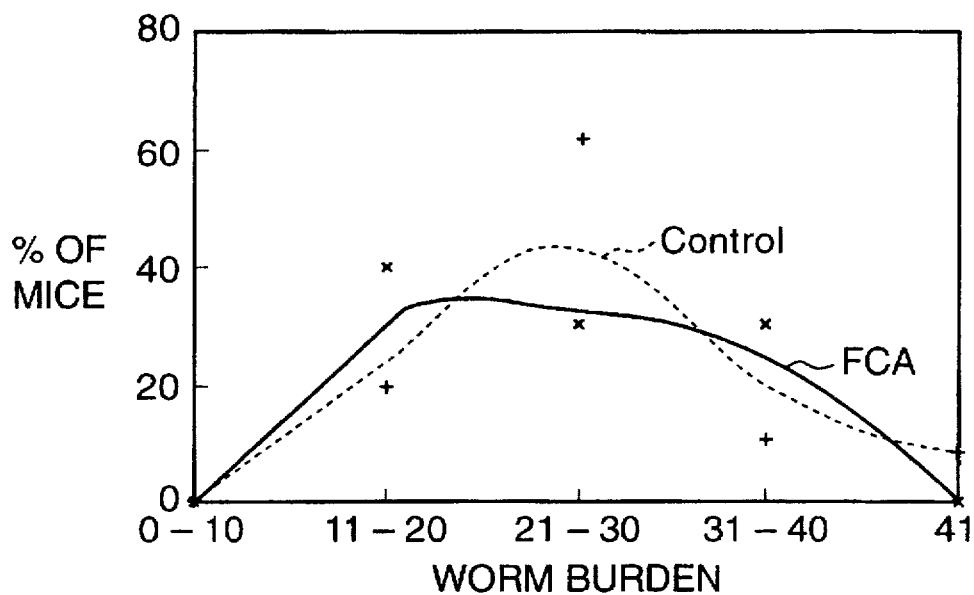
Figure 5D:
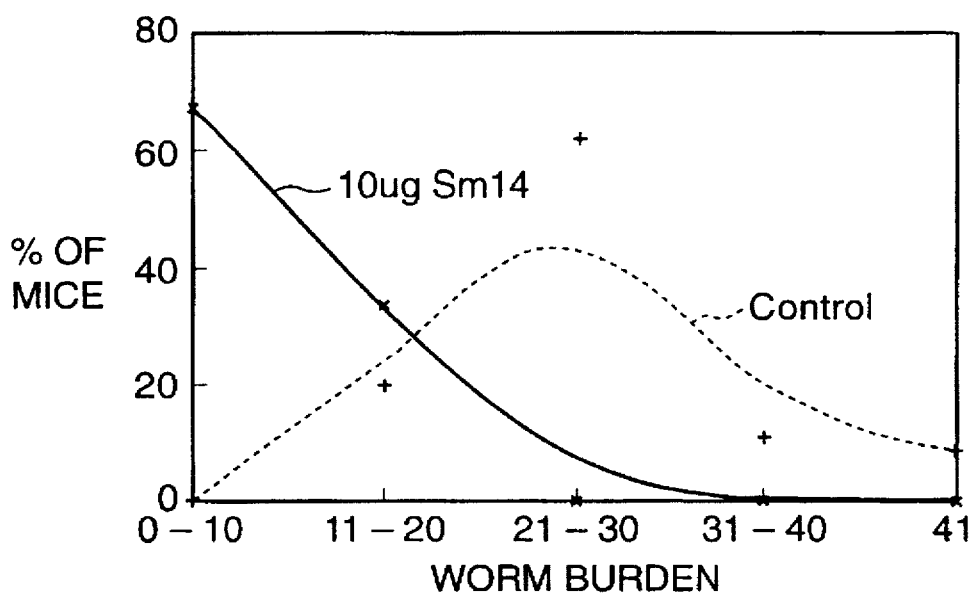
Figure 6A:
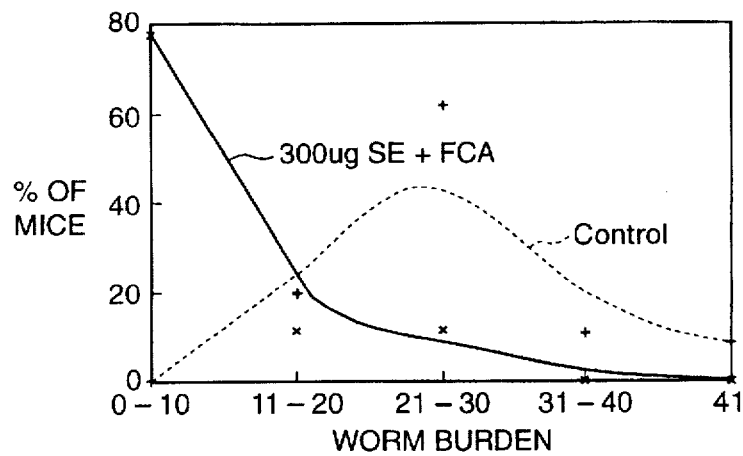
FIGS. 6A, 6B, and 6C show the evaluation of the level of protection of the rSm 14 according to experiment 4.
Figure 6B:
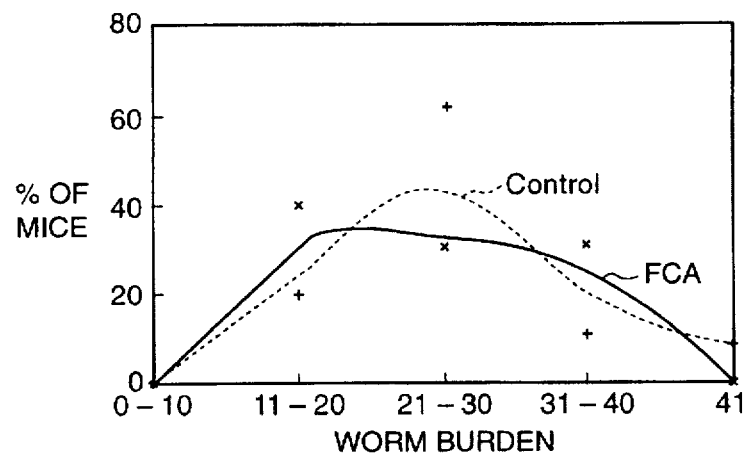
Figure 6C:
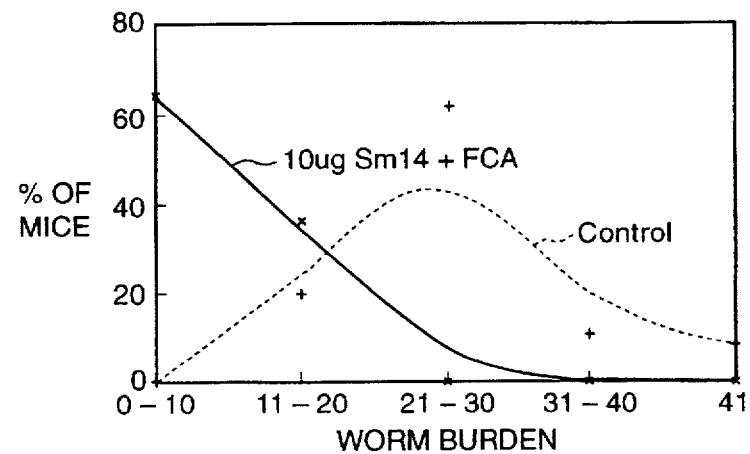

A following reference to FIG. 2 shows the three dimensional structure of Sm 14.

The computer modelling of the structure of Sm-14 according to the present invention is held on the basis of the known high homology of Sm-14 with proteins for which the crystal structure has been already determined. This gives a detailed and reliable three-dimensional structure of Sm-14 to be modelled by computer modelling.

The three-dimensional structure teaches that: (1) Sm-14 is a barrel shaped protein; (2) the fatty acid binds within the barrel; (3) the barrel is formed by ten beta pleated sheets; (4) the sheets are joined by shorts loops; (5) the loops exhibit divergence between members of the family of fatty acid binding proteins and is responsible for the antigenicity of Sm-14.

EXAMPLE 2

Example 2 includes experiments 1 to 4. The protocols of experiments 1 to 4 were carried out as described below, and they show the protective activity of SE and Sm-14 in Swiss mice.

The immunization protocols with SE (300 ug/ml per dose/animal) and Sm 14 fusion protein (10 ug/ml/dose) were performed with the following immunization protocol which consists of two doses of the antigen, with or without Freund's adjuvant, given to naive mice at intervals of seven days by subcutaneous injection followed by a booster dose 21 days after the second dose. The intervals between the application of the vaccinating doses can be varied. After an intervals of 60 days (which also can be varied, for example 45 days) the animals were challenged with 100 cercariae.

The overall protection for each group of animals (immunized challenged animals and respective controls) was calculated as follows:

$$C-V/C \times 100$$

where C=parasites recovered from controls; and, V=parasites recovered from vaccinated animals.

The results are shown in Table I.

Different control groups characterized by sex and age matched SW mice, simultaneously challenged with the same number and pool of S. mansoni cercariae, were used as infection controls for each individual experiment. These animals received only parallel injections of PBS (Phosphate Buffered Saline). Additional control groups for the fusion protein (gene 10) and the adjuvant (Freund's complete adjuvant) were also included.

In experiment 1, protective activity of rSm-14 with or without adjuvant (FCA) was analyzed in parallel to the activity of gene 10 protein, as can be observed in Table II. Mean worm burdens recovered from mice vaccinated with purified gene 10 protein, with or without FCA, were virtually the same as worm burden harvested from animals of PBS control group.

In experiment 2 the protective activity induced by rSm-14 and rSm-14 with FCA was assayed in comparison to vaccination with SE (with or without FCA).

Experiment 3 and 4 were designed to test the activity of the FCA alone and the reproductibility of protective activity induced by vaccination with rSm-14.

In all experiments the high capacity of rSm-14 to induce significantly high levels of immuno protection against further challenged infection of mice with S. mansoni is conclusively demonstrated.

Statistical analysis of presented data shows that worm burden recovered from the vaccinated groups is significantly lower ($p<0.05$) than mean number of parasites harboured from non-vaccinated—infected animal.

EXAMPLE 3

This example shows a protective activity of SE and rSm-14 in rabbits.

The immunization protocols are the same as those used in Swiss mice in Example 2. The amounts of dose/animal are indicated in Table II. The rabbits were challenged with 1000 cercariae (instead of 100 as in Example 2).

Table II shows the capacity of rSm-14 to induce significantly high levels of immune protection against challenge infection of rabbits with S. mansoni.

Furthermore, this example makes clear the activity of rSm 14 as an isolated antigen in comparison with the SE mixture.

The results are shown in Table II.

EXAMPLE 4

This example demonstrates experiments 1 to 4 of Example 2 (which means that the same immunization protocols were used) but with a different methodology to evaluate protection.

This methodology is based on the establishment of vaccine-induced resistance, by means of a populational analysis of worm burdens frequencies through the distribution of worm burdens in a series of parasite ranges.

The results are shown in Table III.

According to Table III purified recombinant Sm-14 stimulated a level of protection that was not significantly different from that of intact SE as judged by mean levels of worm burden (Table 1). The levels of protection achieved with SE are consistent with previously published results. Of particular interest is the fact that a similar level of protection is achieved with or without adjuvant which bodies well for the use of the antigen in humans. In addition, the fact that we successfully protected groups of outbred Swiss mice with the antigen shows that genetic restriction of the immune system does not result in gross variations of the protective response.

As can be seen in Table III, completely different patterns of worm burden distribution were observed in the vaccinated versus non-vaccinated groups. Particularly striking is the difference in the number of mice in the group with 0–10 worms. Following a challenge infection of 100 cercariae/mouse none of the non-vaccinated mice had levels of infection in this range and peak of frequency (60%) for infected (non-vaccinated) animals was in the range of 21–30 worms. In contrast, the peak of frequency (64.5%) for mice vaccinated with either SE or Sm-14 fell within the range of 0–10 worms/mouse.

As can be seen, according to the present invention, it is of particular interest that essentially the whole of the protective effect of the complex SE mixture can be reproduced with this single antigen. Trials with other defined antigens derived from SE (glutathione-S-transferase and paramyosin) did not result in the same high level of protection. As mentioned above Sm-14 also has a significant level of homology with various fatty acid binding proteins.

The results shown in Table III of experiments 1 to 4 are demonstrated graphically in FIGS. 3 (3A, 3B, 3C and 3d) 6 (6A, 6B and 6C).

FIGS. 3 (3A, 3B, 3C and 3d) to 6 (6A, 6B and 6C) correspond to experiments 1 to 4. In these figures it is possible to evaluate the protection through the analysis of the population profiles of the worm burden of vaccinated versus non-vaccinated groups.

Figure 7A:
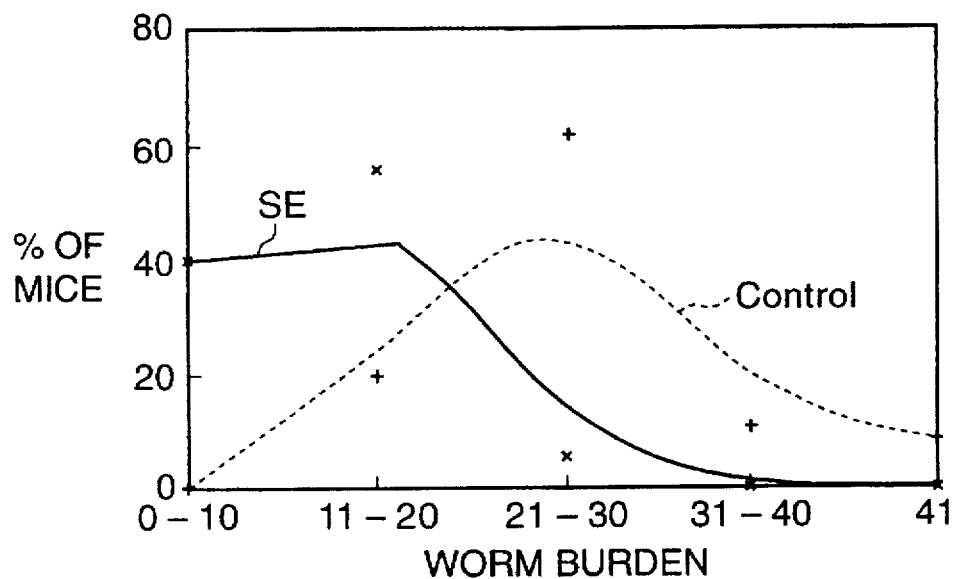
FIGS. 7A and 7B show the pooled results of experiments 1, 2, 3 and 4.
Figure 7B:
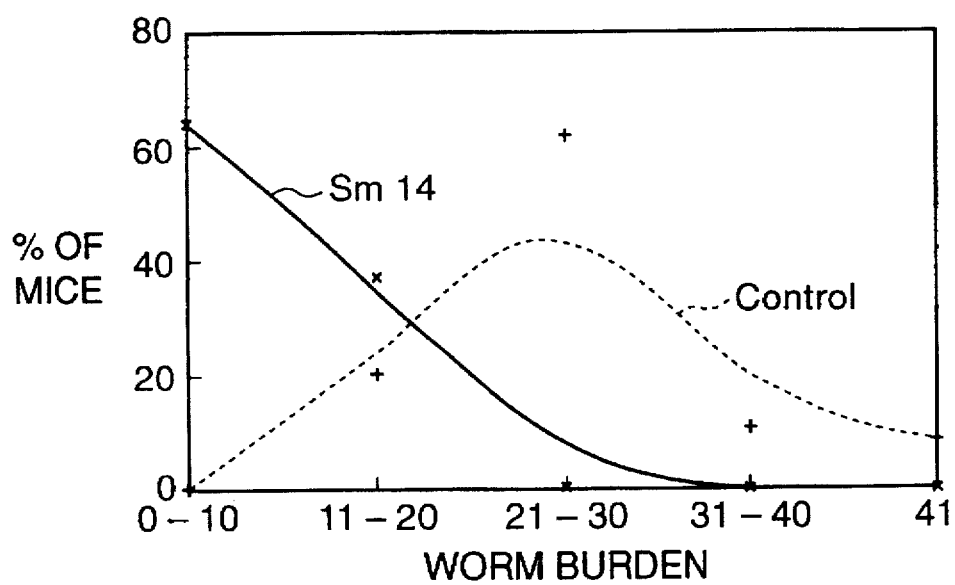
Figure 8A:
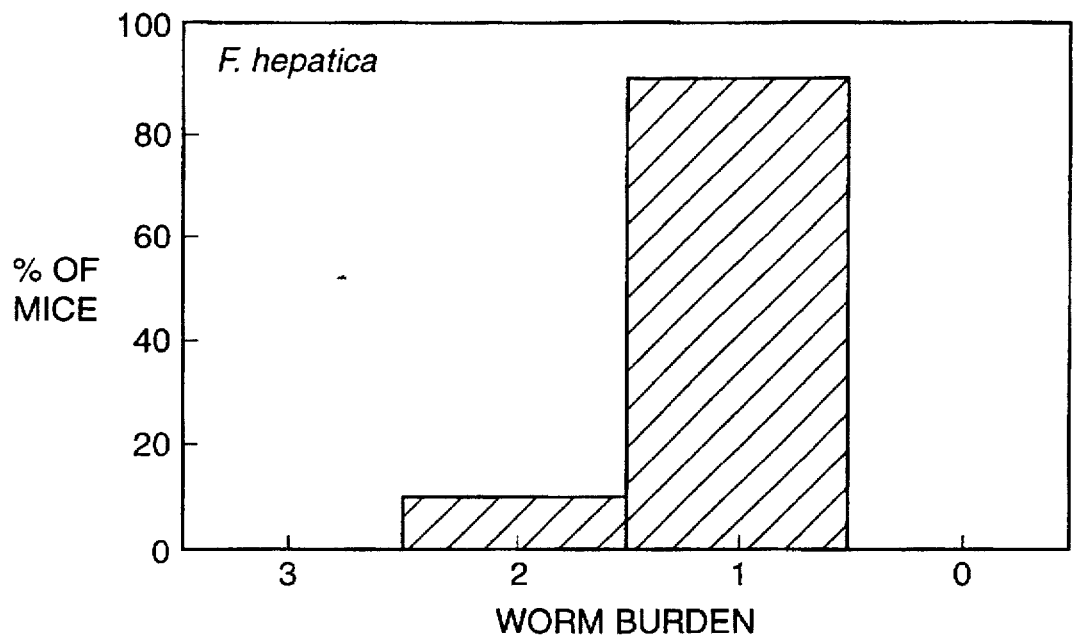
FIGS. 8A and 8B show the vaccination of Swiss mice with rSm 14 against infection with Fasciola hepatica.
Figure 8B:
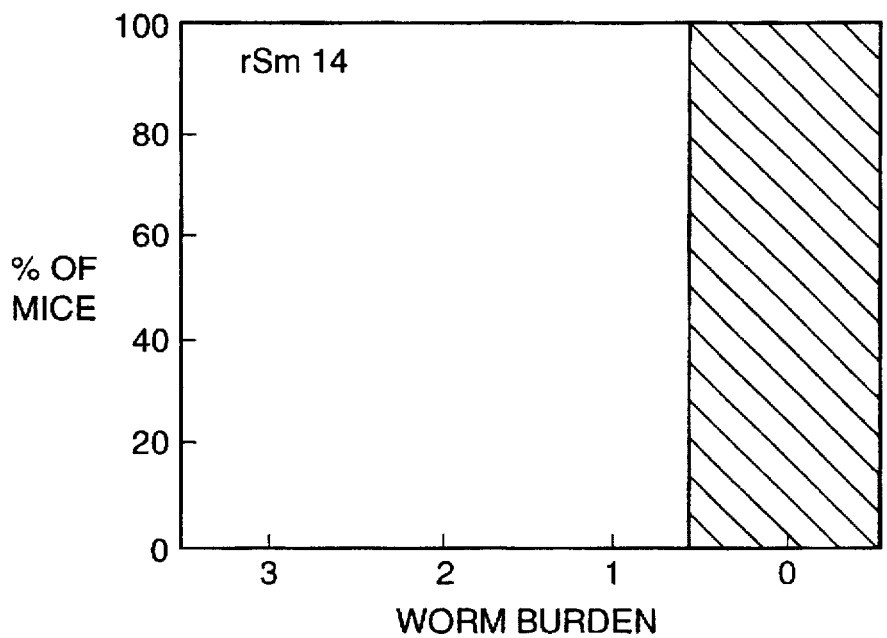

FIGS. 7A and 7B show pooled results.

EXAMPLE 5

In this Example vaccinated mice were challenged with 500 and 1000 cer./animal or challenged 2 or 3 times (100 cerc./animal/infection) with one week interval between each. As can be noted size and number of challenge infections is varied.

The protection induced by three 10 ug doses of protein (rSm 14) injected, remains higher than 50% against a 500 or 1000 cerc./animal single challenge infection. The same effect is observed when the 100 cerc./animal challenge infection is repeated two or three times keeping a one week interval between each one.

The protocols for this Example are as follows.

The data of Example 5 are summarized in Tables IV and V, respectively.

EXAMPLE 6

To demonstrate the reactivity of sera from schistosomiasis patients against fatty acid binding protein from *Schistosoma mansoni*—rSm-14, the Example is carried out as follows.

The sera from human patients from a Brazilian endemic area and sera from young men living out of the endemic area is tested by immunobloting against the recombinant Sm-14 antigen. Patients are classified in groups according to clinical form and eggs are counted. Parsitological diagnosis is achieved by Kato-Katz method.

The results show that sera from all infected individuals recognized rSm-14 in immunobloting, independently of age, worm burden or clinical form, thus reflecting the immunogenicity of rSm-14.

EXAMPLE 7

This Example shows the vaccination of Swiss mice with rSm-14 against infection with *Fasciola hepatica* and complete protection achieved against Fasciolosis.

Example 7 was carried out as follows.

Two groups of 15 mice were immunized with rSm-14 with or without adjuvant. The protocol of vaccination is: (a) two weekly injections of antigen (10 ug/dose/animal rSm 14) emulsified or not in FCA (adjuvant); (b) applying a new dose of injection of antigen three weeks later; and, (c) forty five days after the third dose they were challenged with three *Fasciola hepatica* metacercariae and sacrificed thirty days after infection.

This Example shows cross-reactive protective antigens between different helminths as Schistosomes and *Fasciola hepatica*.

It was recently reported that an antigen named FSh15 cloned from the related parasite, the liver fluke *Fasciola hepatica*, has significant level of homology at the level of predicted amino acid sequence with Sm-14 and present results showing Sm 14 to be the homologue of this protein in *Fasciola hepatica*.

Recombinant Sm-14 was thus tested as a vaccinating antigen against *Fasciola hepatica* infection as described in this Example.

Figure 9:
FIG. 9 shows the liver of a non-vaccinated animal which was infected with Fasciola hepatica.
Figure 10:
FIG. 10 also shows the liver of a non-vaccinated animal which was infected with Fasciola hepatica.
Figure 11:
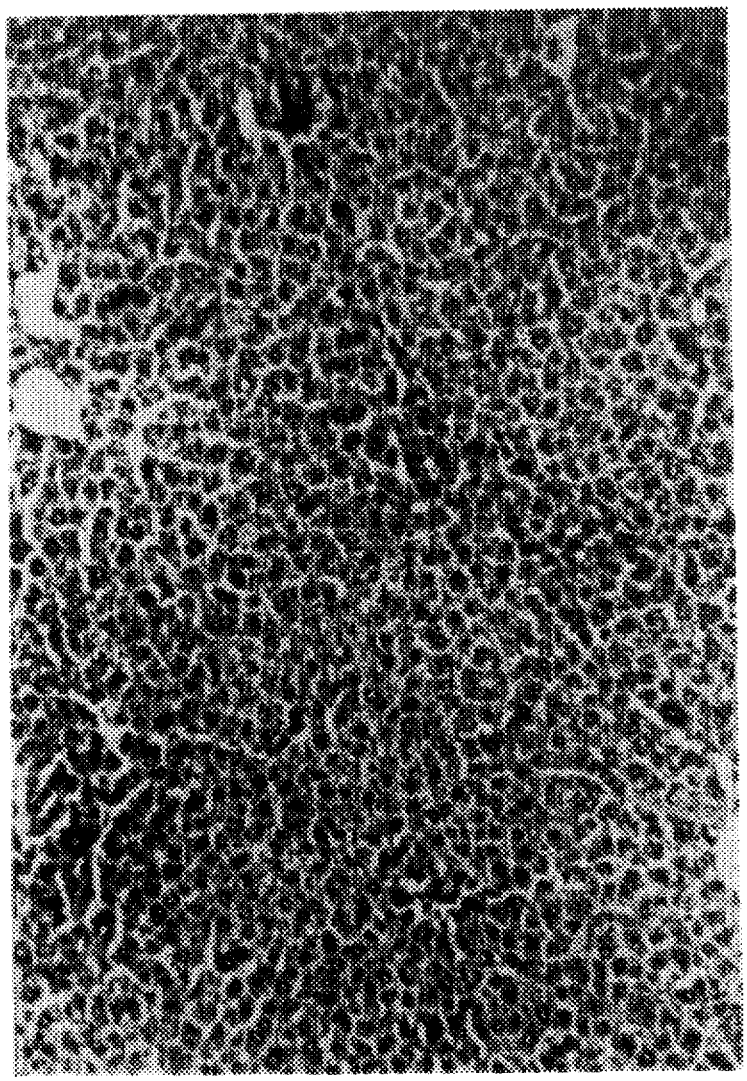
FIG. 11 shows the liver of a vaccinated animal which was infected with Fasciola hepatica.

References to FIGS. 9, 10 and 11 will follow, showing the liver of non-vaccinated (FIGS. 9 and 10) versus vaccinated animals (FIG. 11).

After the parasitological test to evaluate the infection by the *Fasciola hepatica* of the rSm 14 vaccinated and non-vaccinated (controls) animals, subjected to the same infection with three metacercarie/mouse, the liver, intestines and other organs were examined by classical histological processes to evaluate the pathology which developed in the animals of the two groups. It should be pointed out that mainly the liver and the intestines are the most affected organs by the *Fasciola hepatica* and, therefore, they were extensively examined.

Thus, thirty days after oral infection by the classical method with three metacercarie of *Fasciola hepatica* per mouse, the animals were sacrificed for an evaluation of the infection burden acquired in the presence of the previous vaccination with rSm 14 as compared to non-vaccinated animals. The organs were fixed in Milloning solution, cut, stained by the Hematoxylin-Eosin technique, and examined under the optical microscope.

It is conclusively demonstrated by means of FIGS. 8A, 8B, 9, 10 and 11 that rSm-14 is capable of inducing protection against *Fasciola hepatica* infection on the basis of parasitological and anatomopathological data. Out of the rSm-14 vaccinated animals virtually no individual acquired the infection, after exposure to three (maximum dose allowed for mice) metacercarie of *Fasciola hepatica*. On the contrary all non-vaccinated control animals became infected after the same exposure.

From the anatomopathological point of view, the liver parenchryma of all individuals that were vaccinated with rSm-14 did not show any alteration related to *Fasciola hepatica* infection except for small fibrotic areas at the level of Glisson capsule. This finding shows that the challenging parasites have been killed by effect of vaccination, very early in their life cycle at the vertebrate host. On the contrary all the non vaccinated/infected animals exhibited extensive areas of destruction of hepatocytes with severe hemorragical regions that were extensive until Glisson capsule.

As can be seen in FIGS. 9 and 10 extensive destruction of parenchryma was observed together with the presence of the adult parasites in several individuals.

TABLE I

PROTECTIVE ACTICITY OF SE AND rSm 14 IN SWISS Mice

|  | Immunization Antigen ( 3 doses) | n° of mice | Worm Burden | Protection % |
|---|---|---|---|---|
| Exp 1.: | 10 ug Sm 14 + FCA | 20 | 12.1 | 50.6 |
|  | 10 ug Sm 14 | 19 | 9.9 | 59.6 |
|  | 10 ug Gene 10 + FCA | 22 | 28.4 | 0 |
|  | 10 ug Gene 10 | 22 | 27.7 | 0 |
|  | PBS | 12 | 24.5 | 0 |
| Exp 2.: | 300 ug SE + FCA | 21 | 7.8 | 72.1 |
|  | 300 ug SE | 20 | 12.9 | 53.9 |
|  | 10 ug Sm 14 + FCA | 10 | 9.6 | 65.7 |
|  | 10 ug Sm 14 | 14 | 13.6 | 51.4 |
|  | PBS | 8 | 28.0 | 0 |
| Exp 3.: | 300 ug SE + FCA | 11 | 11.6 | 56.7 |
|  | 300 ug FCA | 10 | 25.9 | 0 |
|  | 10 ug Sm 14 + FCA | 11 | 10.1 | 62.3 |
|  | 10 ug Sm 14 | 12 | 8.6 | 67.9 |
|  | PBS | 8 | 26.8 | 0 |
| Exp 4.: | 300 ug FCA | 10 | 23.2 | 0 |
|  | 10 ug Sm 14 + FCA | 9 | 10.1 | 64.0 |
|  | 10 ug Sm 14 | 9 | 12.5 | 55.3 |
|  | PBS | 7 | 28.0 | 0 |

TABLE II

PROTECTIVE ACTICITY OF SE AND rSm 14 IN RABBITS (NEW ZEALAND)

| Immunization Antigen + FCA 3 doses | Number of rabbits | X = sem | Protection (%) |
|---|---|---|---|
| 600 ug SE + FCA | 4 | 7.4 ± 3.9 | 93 |
| 80 ug Sm 14 + FCA | 4 | 12.0 ± 4.1 | 89 |
| Control | 4 | 109.5 ± 11.0 | — |

TABLE III

Protective Activity of rSm 14 in outbred mice Distribution of Worm Burden Frequency

Experiment 1

| Worm Burden | Sm14 + FCA | Sm 14 | Gene 10 + FCA | Gene 10 | Control (PBS) |
|---|---|---|---|---|---|
| 0–10 | 65.0 | 57.9 | — | — | — |
| 11–20 | 20.0 | 31.6 | 4.5 | — | 19.7 |
| 21–30 | 15.0 | 10.5 | 59.1 | 68.2 | 61.7 |
| 31–40 | — | — | 31.8 | 27.3 | 10.5 |
| 41 | — | — | 4.5 | 4.5 | 8.1 |
| N = mice/gp | 20 | 19 | 22 | 22 | 88 |

Experiment 2

| | SE + FCA | SE | Sm14 + FCA | Sm14 | Control (PBS) |
|---|---|---|---|---|---|
| 0–10 | 76.2 | 40.0 | 60.0 | 35.7 | — |
| 11–20 | 23.8 | 55.0 | 40.0 | 64.3 | 19.7 |
| 21–30 | — | 5.0 | — | — | 61.7 |
| 31–40 | — | — | — | — | 10.5 |
| 41 | — | — | — | — | 8.1 |
| N = mice/gp | 21 | 20 | 10 | 14 | 88 |

Experiment 3

| | SE + FCA | FCA | Sm14 + FCA | Sm14 | Control (PBS) |
|---|---|---|---|---|---|
| 0–10 | 77.8 | — | 63.6 | 66.7 | — |
| 11–20 | 11.1 | 40.0 | 36.4 | 33.3 | 19.7 |
| 21–30 | 11.1 | 30.0 | — | — | 61.7 |
| 31–40 | — | 30.0 | — | — | 10.5 |
| 41 | — | — | — | — | 8.1 |
| N = mice/gp | 9 | 10 | 11 | 12 | 88 |

Experiment 4

| | FCA | Sm14 + FCA | Sm14 | Control (PBS) |
|---|---|---|---|---|
| 0–10 | — | 44.4 | 22.2 | — |
| 11–20 | 40.0 | 44.4 | 77.8 | 19.7 |
| 21–30 | 30.0 | 11.2 | — | 61.7 |
| 31–40 | 30.0 | — | — | 10.5 |
| 41 | — | — | — | 8.1 |
| N = mice/gp | 10 | 9 | 9 | 88 |

TABLE IV

PROTECTIVE ACTIVITY OF rSm IN OUTBRED MICE AS A FUNCTION OF VARIATION OF CHALLENGE INFECTION
VACCINATION WITH Sm14 + FCA AGAINST DIFFERENT INFECTIONS

| GROUPS | NUMBER OF MICE | NUMBER OF CERCARIAE/MICE | X ± SEM | PROTECTION (%) |
|---|---|---|---|---|
| 1 | 20 | 1.000 | 58 ± 13.2 | 65.9 |
| CONTROL | 20 | 1.000 | 170 ± 15.0 | — |

TABLE IV-continued

PROTECTIVE ACTIVITY OF rSm IN OUTBRED MICE AS A FUNCTION OF
VARIATION OF CHALLENGE INFECTION
VACCINATION WITH Sm14 + FCA AGAINST DIFFERENT INFECTIONS

| GROUPS | NUMBER OF MICE | NUMBER OF CERCARIAE/MICE | X ± SEM | PROTECTION (%) |
|---|---|---|---|---|
| 2 | 20 | 500 | 31.5 ± 2.3 | 49.7 |
| CONTROL | 20 | 500 | 62.6 ± 2.1 | — |

IMUNIZATION SCHEME: X3 DOSES: 10 µg OF rSm14 + FCA WITH 1 WEEK INTERVAL,
CHALLENGE INFECTION, 45 DAYS AFTER THE LAST VACCINATION DOSE. $P < 0.05$

TABLE V

PROTECTIVE ACTIVITY OF rSm 14 IN OUTBRED MICE AS A FUNCTION
OF MULTIPLE CHALLENGE INFECTIONS.
VACCINATION WITH SM14 + FCA AGAINST DIFFERENT INFECTIONS

| GROUPS | NUMBER OF MICE | NUMBER OF CERCARIAE/MICE | X ± SEM | PROTECTION (%) |
|---|---|---|---|---|
| 1 | 20 | 100 | 11.2 ± 1.09 | 65.9 |
| CONTROL | 20 | 100 | 27.2 ± 2.2 | — |
| 2 | 20 | 100 (X2) | 33.0 ± 1.7 | 57.3 |
| CONTROL | 20 | 100 | 52.6 ± 1.5 | — |
| 3 | 20 | 100 (X3) | 42.3 ± 2.3 | 59.2 |
| CONTROL | 20 | 100 | 47.3 ± 3.3 | — |

IMUNIZATION SCHEME: X3 DOSES: 10 µg OF rSm14 + FCA WITH 1 WEEK INTERVAL,
CHALLENGE INFECTION, 45 DAYS AFTER THE LAST VACCINATION DOSE. $P < 0.05$

---

We claim:

1. An immunogenic composition able to confer at least partial protection against infection with pathogenic helminths, comprising an effective amount of an isolated SM-14 protein and a pharmaceutically acceptable carrier, wherein the SM-14 protein is a 14 KD fatty acid binding protein of *Schistosoma mansoni*.

2. The immunogenic composition of claim 1, wherein the sequence of the 14 KD protein is SEQ ID NO:1.

3. The immunogenic composition of claim 1, further comprising an adjuvant.

4. The immunogenic composition of claim 3, wherein the adjuvant is Freund's complete adjuvant.

5. A method for inducing at least partial protection against infection with pathogenic helminths, comprising administering to a mammal one or more doses of the comparison of any of claims 1–4.

6. A method for inducing at least partial protection against infection with schistosomes, comprising administering to a mammal one or more doses of the composition of any of claims 1–4.

7. A method for inducing at least partial protection against infection with schistosomes, comprising administering to a mammal one or more doses of the composition of claim 1.

8. A method for inducing at least partial protection against infection with *Fasciola hepatica*, comprising administering to a mammal one or more doses of the composition of claim 1.

9. A method for inducing at least partial protection against infection with pathogenic helminths, comprising administering to a mammal one or more doses of the composition of claim 1 to a mammal, wherein said doses include up to 3 doses of 80 µg or less of SM-14, optionally with an adjuvant.

10. An immunogenic composition able to confer at least partial protection against infection with pathogenic helminths, consisting essentially of an effective amount of an isolated SM-14 protein, a pharmaceutically acceptable carrier, and optionally, an effective adjuvant, wherein the SM-14 protein is a 14 KD fatty acid binding protein of *Schistosoma mansoni*.

11. An immunogenic composition able to confer at least partial protection against infection with pathogenic helminths, comprising an effective amount of isolated rSM-14 protein and a pharmaceutically acceptable carrier, wherein rSM-14 protein is a recombinantly produced protein comprising the sequence of a 14 KD fatty acid binding protein of *Schistosoma mansoni*.

12. The immunogenic composition of claim 11, wherein the sequence of the 14 KD protein is SEQ ID NO:1.

13. The immunogenic composition of claim 11, wherein the rSM-14 protein contains amino acids 1–260 of the major T7 capsid protein fused to SEQ ID NO:1.

14. The immunogenic composition of claim 11, further comprising an adjuvant.

15. The immunogenic composition of claim 14, wherein the adjuvant is Freund's complete adjuvant.

16. The immunogenic composition of claim 11, wherein the amount of rSM-14 is effective to confer at least partial protection against infection with schistosomes.

17. The immunogenic composition of claim 11, wherein the amount of rSM-14 is effective to confer at least partial protection against *Schistosoma mansoni* infection.

18. The immunogenic composition of claim 11, wherein the amount of rSM-14 is effective to confer at least partial protection against *Fasciola hepatica* infection.

19. The immunogenic composition of claim 18, which is a vaccine comprising an amount of rSM-14 effective to prevent *Fasciola hepatica* infection.

20. A method for inducing at least partial protection against infection with pathogenic helminths, comprising administering to a mammal one or more doses of the composition of any of claims 11–19.

21. A method for inducing at least partial protection against infection with schistosomes, comprising administering to a mammal one or more doses of the composition of any of claims 11–16.

22. A method for inducing at least partial protection against infection with *Schistosoma mansoni*, comprising administering to a mammal one or more doses of the composition of claim 17.

23. A method for inducing at least partial protection against infection with *Fasciola hepatica*, comprising administering to a mammal one or more doses of the composition of claim 18.

24. A method of preventing infection with *Fasciola hepatica* in a mammal, comprising administering one or more doses of the vaccine of claim 19.

25. A method for inducing at least partial protection against infection with pathogenic helminths, comprising administering to a mammal one or more doses of the composition of claim 11 to a mammal, wherein said doses include up to 3 doses of 80 µg or less of rSM-14, optionally with an adjuvant.

* * * * *

UNITED STATES PATENT AND TRADEMARK OFFICE
CERTIFICATE OF CORRECTION

PATENT NO. : 5,730,984
DATED : March 24, 1998
INVENTOR(S) : TENDLER, et al.

It is certified that error appears in the above-identified patent and that said Letters Patent is hereby corrected as shown below:

In the title: "SM" should be amended to --Sm--;

Column 12, table 1, "Acticity" should be --Activity--;

Claim 5, ln 3, "Comparison" should be amended to --Composition--;

Claim 7, ln 2, "schistosomes" should be amended to --Schistosoma mansoni--; and

Signed and Sealed this

Sixth Day of October, 1998

Attest:

BRUCE LEHMAN

Attesting Officer

Commissioner of Patents and Trademarks